United States Patent [19]

Toth et al.

[11] Patent Number: 4,644,271

[45] Date of Patent: Feb. 17, 1987

[54] METHOD AND APPARATUS FOR EXAMINING A WORKPIECE

[75] Inventors: James M. Toth, Lyndhurst; Richard M. Harris, North Royalton, both of Ohio

[73] Assignee: LTV Steel Company, Inc., Cleveland, Ohio

[21] Appl. No.: 705,149

[22] Filed: Feb. 25, 1985

[51] Int. Cl.[4] .............................................. G01N 27/82
[52] U.S. Cl. ..................................... 324/238; 324/228
[58] Field of Search ............... 324/228, 237, 234, 236, 324/238, 240, 241, 242, 220

[56] References Cited

U.S. PATENT DOCUMENTS

| | | | |
|---|---|---|---|
| 2,938,162 | 5/1960 | Roffman et al. | 324/240 |
| 2,998,566 | 8/1961 | Cochran . | |
| 3,056,081 | 9/1962 | Hochschild . | |
| 3,110,860 | 10/1963 | Allen . | |
| 3,152,302 | 10/1964 | Allen et al. | 324/226 |
| 3,419,797 | 12/1968 | Libby | 324/220 |
| 4,203,069 | 5/1980 | Davis | 324/220 |
| 4,337,431 | 6/1982 | Hale | 324/220 |

FOREIGN PATENT DOCUMENTS

1138962 10/1962 Fed. Rep. of Germany ...... 324/209
565248 2/1974 U.S.S.R. .

Primary Examiner—Reinhard J. Eisenzopf
Assistant Examiner—Robert W. Mueller
Attorney, Agent, or Firm—Watts, Hoffmann, Fisher & Heinke

[57] ABSTRACT

An eddy current inspector for imaging of a workpiece shape. A differentially wound test coil mounted next to a workpiece path of travel is energized with a time varying signal to set up eddy currents in the workpiece. A field modifying sleeve is rotated with the field to periodically disrupt the eddy current inducing field. Two signals from the coil, a flaw signal and a shape signal, are time multiplexed and scaled to present a real time image of a workpiece surface as well as the orientation and severity of flaws existing at the workpiece surface.

17 Claims, 12 Drawing Figures

METHOD AND APPARATUS FOR EXAMINING A WORKPIECE

TECHNICAL FIELD

The present invention relates to an eddy current flaw inspector and more particularly to method and apparatus for imaging of a workpiece shape as the workpiece is inspected.

BACKGROUND ART

Prior art eddy current test apparatus has been utilized for inspecting metallic workpieces for flaws and irregularities. Eddy current testers employ a current carrying coil for inducing eddy currents in a workpiece surface in close proximity to the current carrying coil. To produce these eddy currents, an alternating current signal energizes the test coil causing electromagnetic radiation to impinge on the workpiece surface.

The response of the workpiece to this electromagnetic radiation varies with the structure of the workpiece. Flaws and irregularities in the workpiece modify the eddy currents and these modified eddy currents are monitored to obtain an indication of flaw and/or irregularity locations. Disruptions due to flaws or irregularities in the workpiece can be monitored with a test coil closely positioned in relation to the workpiece surface. In some eddy current applications, the test coil is separate from the energization coil but in certain instances, the test and energization coil are one in the same.

One use of eddy current test apparatus is to detect flaws in a workpiece as that workpiece is produced. In the manufacture of steel bar product, for example, it is advantageous to isolate seams, gaps or other irregularities of a certain severity before large amounts of scrap bar product are produced. This testing must therefore be performed while the bar is still quite hot just after it has been rolled so that corrective measures can be taken to avoid those flaws.

Pending U.S. application Ser. No. 625,029 of Harris et al, which was filed June 27, 1984 and is entitled "Eddy Current Flaw Detector Having Rotatable Field Defining Sleeve", discloses a recent development in eddy current testing. The disclosure of this pending application is incorporated herein by reference. Apparatus disclosed in this application utilizes a rotatable sleeve having apertures which periodically disrupt an electromagnetic field created by an energization coil. Monitoring circuitry coupled to the energization coil analyzes the effect the field disruption has on eddy currents in the workpiece surface. This disruption enhances changes in signal output due to a flaw or the like in the workpiece surface.

Flaw induced variations in energization coil output can be displayed on an oscilloscope. The existence of a flaw in the workpiece surface is exhibited by a spike or other variation in the oscilloscope sweep. Analyzing this type of signal requires skill on the part of the operator of the test unit. The height of the spike is referenced with respect to background signals which vary with noise and irregularities in the shape of the workpiece. The location of the spike along the oscilloscope waveform is not easily interpreted to determine the circumferential location of the flaw on the workpiece surface.

While the Harris et al development represents a significant improvement in eddy current testing for flaws, complete anaylsis of the workpiece condition still requires visual inspection of the workpiece and skill on the part of the operator using the Harris et al apparatus in interpreting the flaw information displayed with that apparatus.

In addition to testing for flaws of a certain depth it is important to recognize when the product is misshaped. An out-of-round steel bar may be scrap even though the product is free of flaws or seams in its outer surface. The specific shape of the misformed workpiece can give an indication of how the problem occurred and what steps can be taken to rectify the problem. The Harris et al apparatus does not address the problem of identifying an irregular or mis-shaped workpiece.

DISCLOSURE OF THE INVENTION

The present invention concerns method and apparatus for generating shape information concerning a workpiece to simplify flaw analysis and evaluation of the condition of the workpiece. The disclosed method can not only show flaw location and severity but also give an accurate picture of the shape and position of the workpiece under study. This capability immediately indicates, for example, when the workpiece is misshapen or asymmetric.

In accordance with the apparatus of the invention, a test coil is mounted next to a workpiece path of travel and coupled to a circuit for electrically energizing the coil. A field modifying member periodically modifies a magnetic field created by the coil. The coil is coupled to a circuit for creating a shape signal relating to a distance between an outer workpiece surface and the coil.

In one embodiment, a shape signal and a separate flaw indicating signal can be time multiplexed and then scaled to provide an indication of flaw depth, flaw location, and workpiece shape. The time multiplexed signals are coupled to apparatus for depicting the workpiece condition as the field modifying means scan the workpiece. Alternately, only the shape or only the flaw signal, appropriately scaled, can be displayed.

In a preferred embodiment of the invention, time multiplexing of the flaw and workpiece information occurs at a rate of 50 times per second. Appropriately scaled signals are used as X and Y components for an oscilloscope display. The 50 hertz repetition rate causes the observer to see both shape and flaw displays simultaneously. Flaws or the like appear as notches in the workpiece and the shape signals depict an outer workpiece circumference.

The scaling circuitry adds information unavailable in the prior art. The scaling circuitry includes an input from a shape and/or a flaw signal generating circuit and scales this signal with a factor related to the orientation of the field modifying means with respect to the workpiece.

The application of this scaling factor is coordinated with rotation of a field modifying sleeve. A test workpiece having a flaw in a particular orientation is scanned and the scaling factors adjusted until the flaw depicted on the oscilloscope screen is the same as the orientation of the flaw on the workpiece.

The disclosed invention simplifies analysis of the workpiece for flaws and the like. An image is presented as the workpiece is scanned so that the appearance of flaws on the image can be readily identified without having to interpret a spike or other irregularly appearing signal on an oscilloscope screen. Off-center positions of the workpiece can be readily spotted since the shape signal gives an indication of the entire workpiece surface.

From the above it should be apparent that one aspect of the invention is improved method and apparatus for displaying an image of the cross-section of an elongated workpiece. This and other objects, advantages and features of the invention will become better understood when a detailed description of a preferred embodiment of the invention is described in conjunction with the accompanying drawings.

BEST MODE FOR CARRYING OUT THE INVENTION

Figure 1:
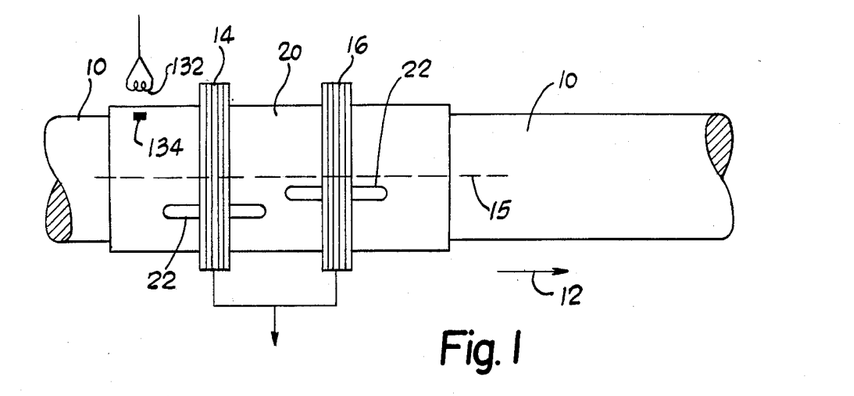
FIG. 1 is a schematic elevation view of a workpiece moving near a probe for analyzing the condition of the workpiece.

Turning now to the drawings, and in particular FIG. 1, an elongated metal workpiece 10 is driven in a direction indicated by an arrow 12 past a test head supporting two differentially wound energization and detection coils 14, 16. Apparatus for moving the workpiece past the detection coils 14, 16 is disclosed in the referenced and incorporated application to Harris et al.

A stainless steel shield 20 is rotatably supported about the workpiece path of travel so that two slots or apertures 22 in the shield rotate beneath the differentially wound coils. The coils are energized with the high frequency signal which sets up magnetic fields in the vicinity of the workpiece 10. The shield 20 is rotated about the workpiece as the detection coils are energized so that the apertures or slots 22 periodically disrupt this magnetic field at different locations about the workpiece 10.

The coils 14, 16 are differentially wound so that signals generated due to the presence of flaws or the like on the workpiece surface produce a positive spike from one coil 14 and a negative spike from the oppositely wound coil 16. The apertures or slots 22 are angularly offset with respect to each other so that first a positive and then a negative signal is generated by a flaw on the workpiece surface. Analyzing circuitry 110 (FIG. 4) coupled to the differentially wound coil 14 creates signals suitable for real time imaging of a cross-section of the workpiece.

Figure 7A:
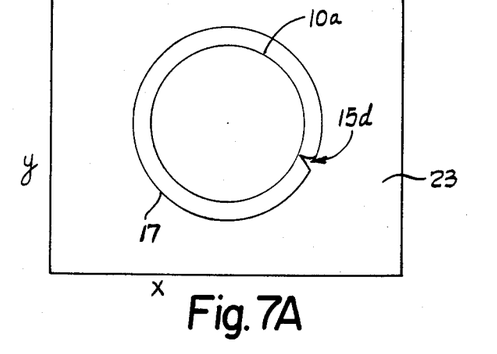
FIGS. 7A-7C are representative images of a workpiece cross-section as depicted on an image screen.

The illustration in FIG. 7A shows the flaw indicating capability of the present invention. In that Figure the shape of the workpiece is viewed on an oscilloscope 23. The shape is acceptable, i.e. forms a uniform circle in cross-section but a deep flaw 15 exists at the workpiece surface at an orientation of approximately 120° from the vertical.

Figure 7B:
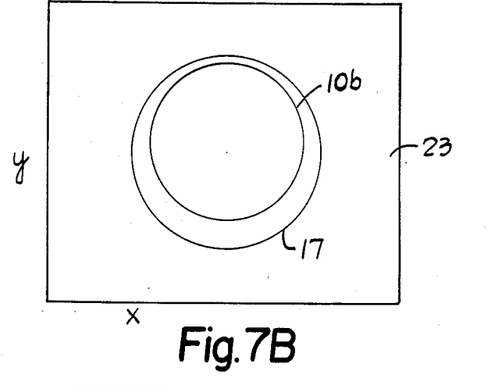

Turning now to FIG. 7B, a different analyzing capability of the invention is displayed on the oscilloscope 23. It is seen that a cross-section of the workpiece 10 approximates a circle. The workpiece 10, however, is mis-centered within the sleeve 20. This would indicate a defect or mis-adjustment in apparatus for moving the workpiece past the coils and suggest maintenance and/or modification of the apparatus to center the workpiece is in order.

Figure 7C:
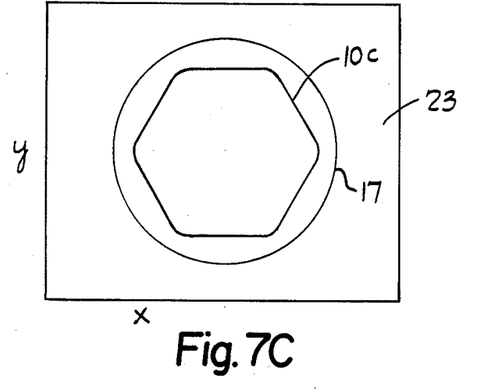

The FIG. 7C illustration shows a hexagonal shaped bar centered within the sleeve 20. If the shape of the bar were non-uniform with excessively rounded corners, for example, this would be apparent. Also, if the bar is to be circular yet appears to be rectangular with rounded corners this defect will be apparent and corrective measures can be taken.

Viewing these representations, the operator of the apparatus can readily ascertain the existence of a flaw and a non-uniform or a non-centered workpiece without examining hard to interpret signal variations on an oscilloscope sweep.

The FIGS. 7A-7C representations are created with the aid of the circuitry 110 (FIG. 4) which generates X and Y deflection inputs to an oscilloscope 23. The circuitry 110 generates one signal representing a distance between one coil 16 and the workpiece surface as the slotted sleeve 20 rotates about the workpiece and generates a second signal representing flaw location and depth. The two signals are time multiplexed and scaled by a factor indicating the instantaneous orientation of the sleeve with respect to the workpiece.

Figure 4:
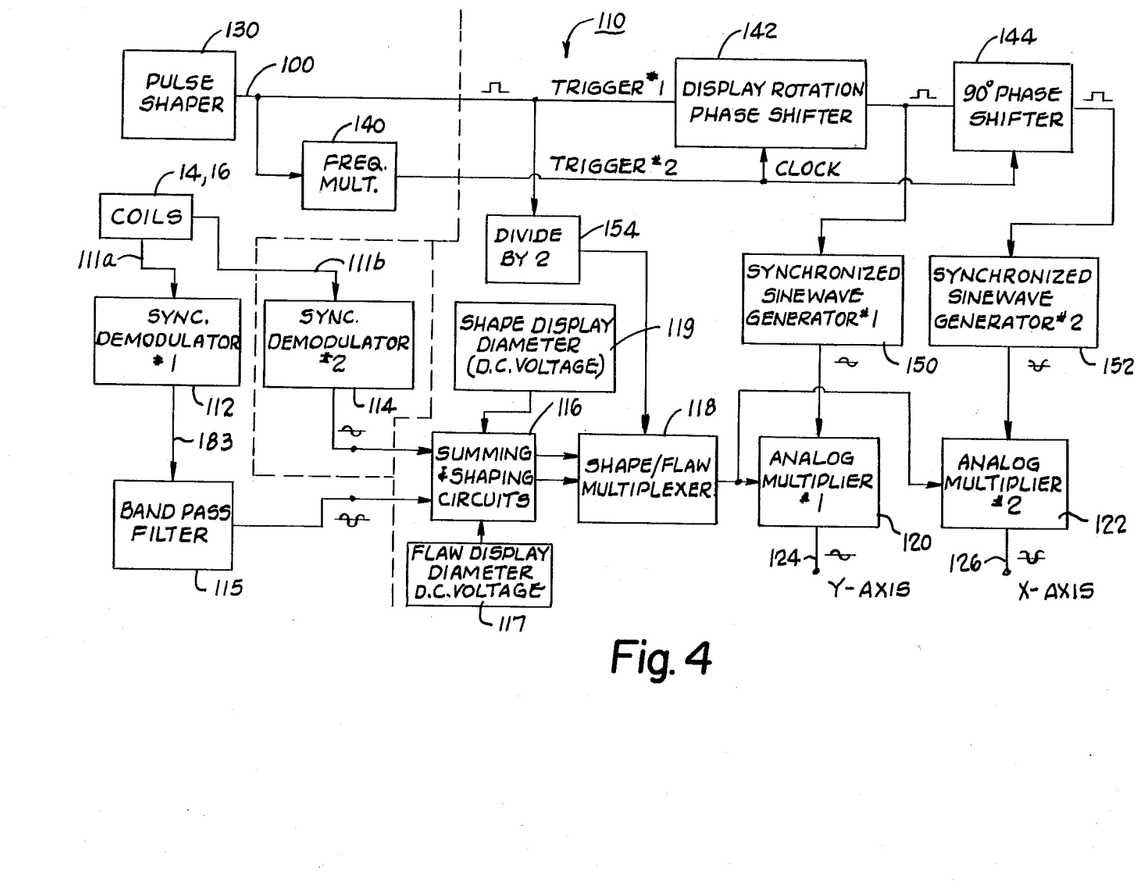

FIG. 4 presents an overview of the analyzing circuitry 110. Two outputs 111a, b from the detection coils 14, 16 are coupled to first and second demodulator circuits 112, 114. The output from one demodulator circuit 112 is flat when no flaw exists on the workpiece surface and is a pulse or spike when a seam or flaw is detected. The height of the pulse represents flaw depth.

A distance between the coil 16 and the workpiece surface is represented by the output from the second demodulator circuit 114. The magnitude of this signal is related to a distance between the coil 16 and workpiece surface at the circumferential position of the aperture 22 beneath the coil 16. A flat response from the demodulator 114 indicates a uniform circular crosssection bar centered within the sleeve.

A summing and shaping circuit 116 halfwave rectifies the signal from the demodulator circuit 112 after those signals pass through 1 kilohertz bandpass filter 115. The rectified output is combined with a D.C. signal from a voltage source 117 proportional to an outside diameter of the workpiece. In an analogous manner the signal from the demodulator 114 is level shifted with a D.C. bias from a second voltage source 119. Subsequent to this D.C. level shift the two outputs are coupled to a multiplex unit 118 which alternates first a flaw indicative signal and then a workpiece shape indicative signal. The multiplexed signals are each coupled to two analog multiplier circuits 120, 122 having outputs 124, 126 coupled to the oscilloscope 23.

Synchronization and timing is provided to the X and Y deflection controls by a pulse shaper 130 coupled to a detection coil 132 (FIG. 1) which monitors rotation of a magnetic device 134 connected to the rotating sleeve 20. This pulse shaper circuit 130 receives spike inputs from the detector coil 132 and shapes those spikes into a square wave pulse. A multiplier circuit 140 is synchronized by an output from the pulse shaper 130 and generates 128 equally spaced pulses between receipt of each pulse shaper signal. An output from frequency multiplier 140 is used as a clock input to two phase shifter circuits 142, 144. The output from the pulse shaper triggers the first phase shift circuit 142 which in turn triggers an output to a synchronized sine wave generator 150 which provides a scaling input to the first analog multiplier 120. A delay applied by the first phase shifter can be programmed to be between 0 and 64 clock pulses as defined by the frequency multiplier 140. This delay allows the location of a flaw to be accurately depicted on an image screen. The second phase shifter 144 generates pulses 90° of sleeve rotation out of phase with respect to the first phase shifter 142. This delay or phase shift synchronizes a second sine wave generator 152.

On alternate revolutions of the shield, first the shape and then the flaw signal is transmitted by the multiplexer 118. The timing of this transmission is controlled by a bi-stable flip flop 154 clocked by the output from the pulse shaper 130. If the sleeve rotation is 100 hertz then the shape and flaw signals are each presented by the multiplexer 118 fifty times per second.

Scaling these real time signals with a sine function at the first analog multiplier 120 results in a continuous output 124 of the form F sine $\theta$ and S sin $\theta$ where F is the flaw signal and S the shape signal. This scaled signal is coupled to Y axis deflection control to an oscilloscope and represents the instantaneous Y component of the workpiece diameter if the shape signal is being displayed or the Y axis compoment of a flaw depicting signal if the flaw signal is displayed. At a rate of 50 hertz the human eye perceives both displays so that both flaw and shape signals appear on the screen.

The 90 degree phase shift by the phase shifter 144 triggers the second sinewave generator 152 to produce an input to the multiplier 122 which is scaled with the output from the multiplexer 118 to produce an output 126 of the the form F cos $\theta$ and S cos $\theta$. This signal serves as the X deflection oscilloscope control. The result of this scaling and deflection control by the multipliers 120, 122 is a two dimensional image synchronized with the rotation of the sleeve to present real time representations (FIGS. 7A-7C) of a cross-section of the workpiece.

The phase shift circuit 142 allows the image to be adjusted empirically until the orientation of flaws in a test workpiece are properly oriented on the display. By suitably delaying the scaling signals the flaw orientation is rotated around the image.

Figure 2:
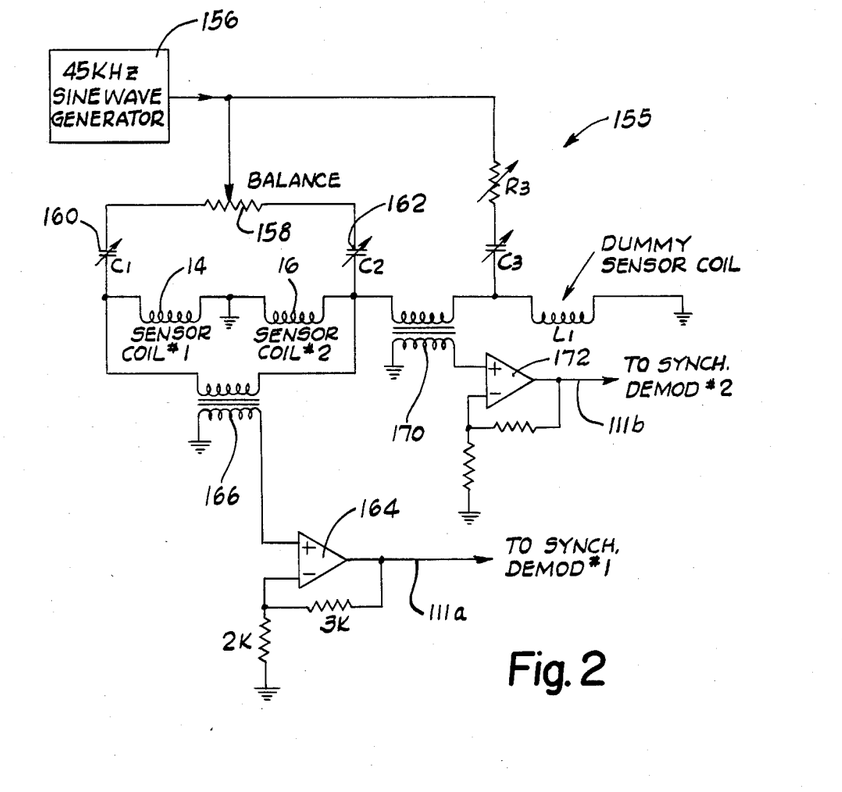
FIGS. 2-6 are electrical schematics of circuitry for analyzing signals from the probe and for producing control signals used in generating the images of the workpiece shape.

An energization and detection circuit 155 for the coils 14, 16 is shown in FIG. 2. A 45 kilohertz lator 156 drives the coils 14, 16 through a balancing resistor 158 and two variable capacitors 160, 162. A signal across the two coils 14, 16 is coupled to an operational amplifier 164 through a transformer 166. An output from the operational amplifier 164 is coupled to the first demodulator 112. A second transformer 170 and operational amplifier 172 couple the signal across one coil 16 to the second demodulator 114.

Figure 3:
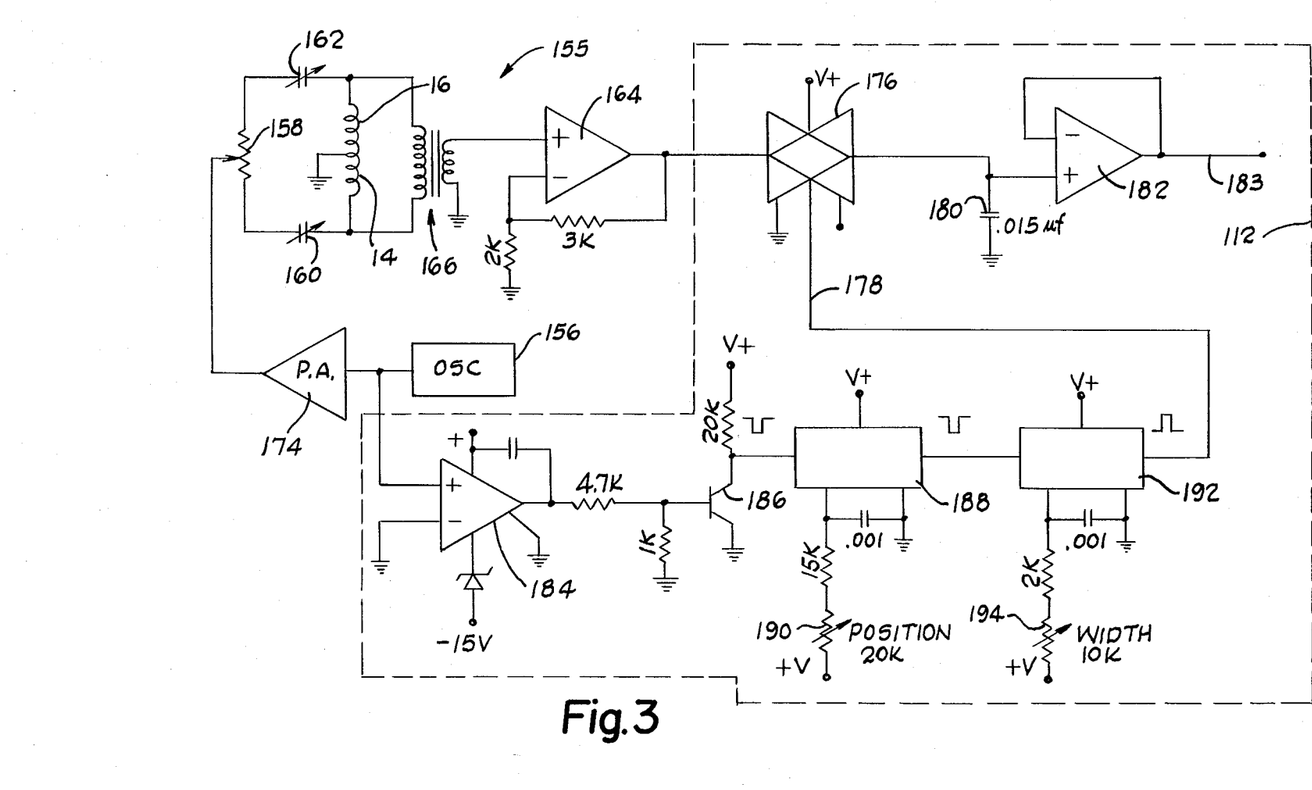

Referring to FIG. 3, a portion of the interface 155 is shown coupled to the demodulator 112. The oscillator 156 drives a power amplifier 174 which in turn is coupled to the two differentially wound coils 14, 16. Interposed between the power amplifier 174 and coils are the variable resistor 158 and two tuning and phase shifting variable capacitors 160, 162. These components allow the relative magnitude and phase of the alternating signals across the coils 14, 16 to be adjusted to enhance sensitivity of the flaw sensing. The oscillator frequency is adjustable and in a preferred embodiment is adjusted to produce a sinusoidal ouput having a frequency of approximately 45 kilohertz. This energization of the two coils sets up magnetic fields which induce eddy currents at the surface of the workpiece.

When these eddy currents are disrupted by the presence of a flaw, the self induced current through the coils is also disrupted. The interaction of the fields with the sleeve and a workpiece flaw results in a spike or a pulse output from the coils 14, 16 which is sensed by a primary of the transformer 166. The output from a secondary of the transformer 166 is coupled to the amplifier 164 which has an output coupled to an analog switch 176 in the demodulator circuit 112. The analog switch 176 has a gate input 178 which selectively transmits signals through the switch 176 to a capacitor 180 and buffer amplifier 182. An output 183 from this buffer 182 is transmitted to the filter circuit 115.

A gate signal for the analog switch originates at the oscillator 156. The gate signal is a pulse which periodically couples the analog gate input to its output. An output from the oscillator 156 is coupled to a comparator 184 which transmits a positive portion of the alternating current signal from the oscillator 156 to a switching transistor 186 for converting the analog output from the oscillator 156 into a series of pulses. A first one shot 188 produces a delay in these pulses of from 7 to 16 microseconds depending on the setting of a variable 20 k resistor 190. A second one shot 192 varies the width of its output pulse from one to five microseconds depending on the setting of a 10 k variable resistor 194.

A 40 kilohertz oscillator output produces a time or period between peak-to-peak signals of 25 microseconds. The ability to shift and shape the gating signal within this 25 microsecond period allows the user to maximize the output and sensitivity of the flaw detection. The signal from the amplifier 182 is a voltage output whose magnitude varies with the presence of a flaw.

The filter circuit 115 comprises four integrated circuits, each having four operational amplifiers for a total of sixteen operational amplifiers. The filter circuit is divided into a high pass filter and a low pass filter with the first eight operational amplifiers making up the high pass filter and the next eight operational amplifiers making up the low pass filter. In a preferred embodiment of the invention, these filters in combination attenuate all signals having frequencies less than or greater than approximately one kilohertz. In this way extraneous signals in the noisy environment of a steel production facility are eliminated and only signals generated by flaws in the workpiece will be transmitted to the summing and shaping circuit 116.

Figure 5:
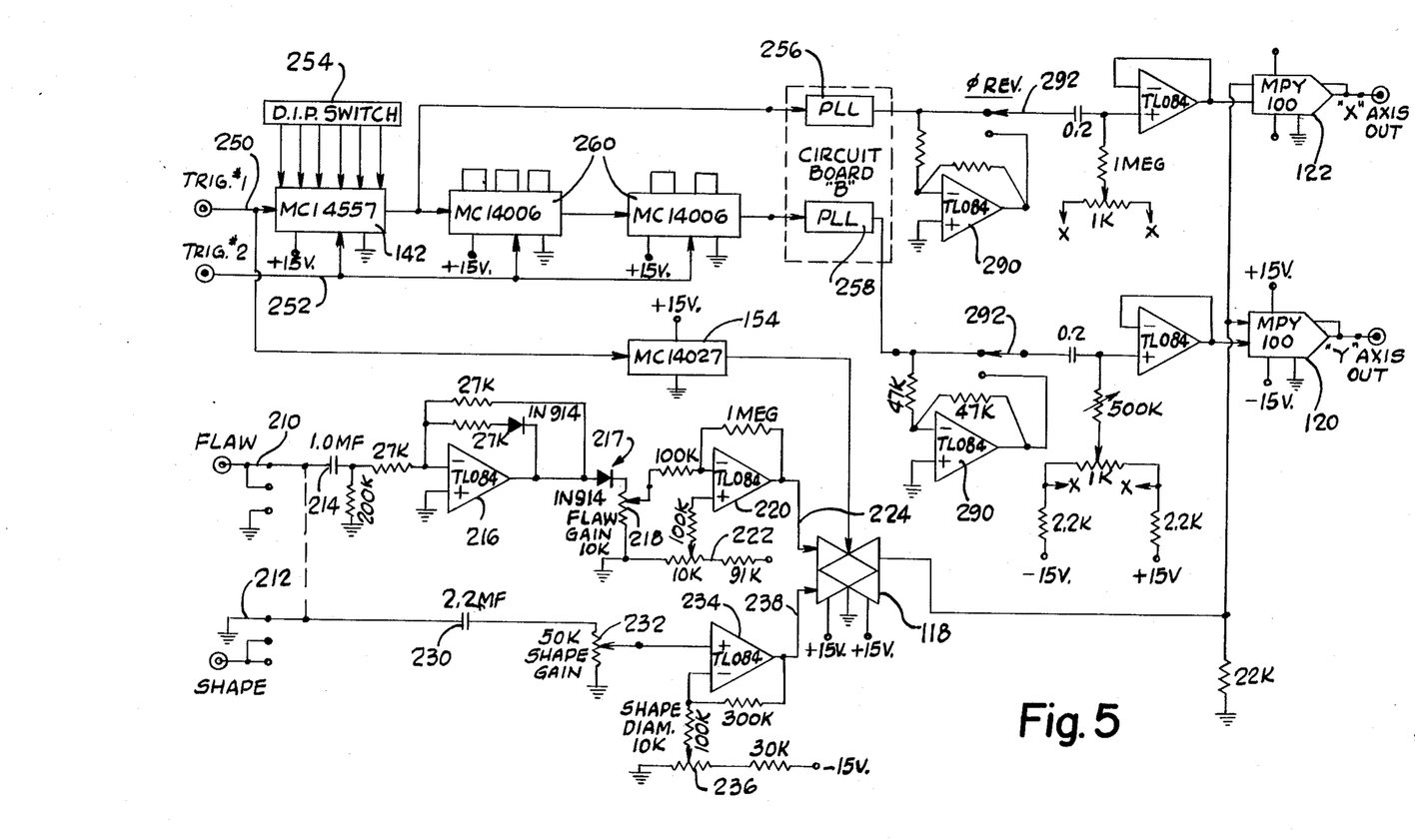
Figure 8A:
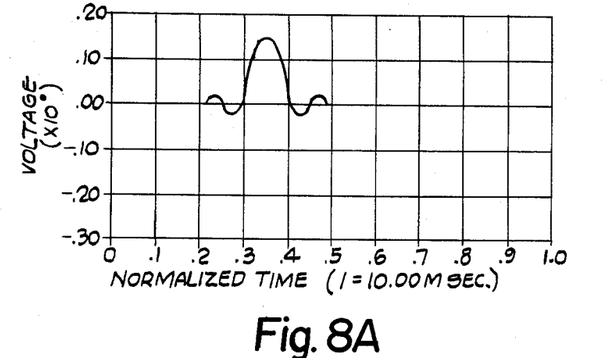
FIGS. 8A-8C illustrate probe output waveforms for generating the FIGS. 7A-7C images.

FIG. 5 shows in greater detail the circuitry of FIG. 4. Two inputs 210, 212 receive flaw and shape information respectively from the two demodulator circuits 112, 114. A representative flaw signal is illustrated in FIG. 8A and is seen to include a relatively flat response with a large pulse centered at the flaw location. This typical flaw signal might for example be the output from a circular workpiece having a single elongated flaw 15 (FIG. 1) extending along its length. This flaw signal is coupled through a coupling capacitor 214 to an operational amplifier 216. The operational amplifier 216 is configured as a precision rectifier so that negative portions of the FIG. 8A signal are eliminated. An optional diode 217 coupled to the output of the precision rectifier 216 performs a thresholding function to eliminate small positive signals from this output. The end result is a single positive pulse having a height related to the depth of the flaw. The size of this pulse is adjusted with a flaw gain potentiometer 218 having an output coupled to the inverting input of a operational amplifier 220.

The amplifier 220 operates as a summing amplifier. A D.C. level shift is added by the voltage source 117 which is preferably a variable potentiometer 222, to the non-inverting input of the operational amplifier 220. The output 224 from this amplifier is a signal of constant magnitude unless a pulse generated by a flaw at the workpiece surface is encountered at which point the magnitude of the ouput is decreased by an amount proportional to the flaw depth. Therefore one input 224 to the multiplex unit 118 is a time varying signal having an information content depicting both location and severity of a flaw in the workpiece 10.

The second input 212 contains shape information which is coupled through a coupling capacitor 230 to a shape gain potentiometer 232. This signal is also a time varying signal having a magnitude related to a distance between the coil 16 and a workpiece surface directly beneath the aperture 22 in the sleeve 20. If a uniform cross-section bar of a circular shape is off center as it passes through the rotating sleeve, a time varying signal (FIG. 8B) will be generated since the instantaneous distance between the workpiece surface and the coil in the vicinity of the aperture or slot varies with time. This signal is input to a non-inverting input of an operational amplifier 234 having a second input coupled to the voltage source 119 which is preferably a variable potentiometer 236. The input from this potentiometer is adjustable and can be adjusted to provide a suitable off-set to the shape signal. An output 238 from the operational amplifier 234 is therefore a time varying signal having an instantaneous value related to the distance between the workpiece surface and the coil 16 at the vicinity of the rotating slot in the sleeve. The output from the multiplexer 118 is coupled to the two scaling multiplier units 120, 122 which are commercially available circuits designated MPY 100.

The two trigger signals from the pulse shaper 30 and frequency multiplier 140 are seen as two inputs 250, 252 to the FIG. 5 circuitry. These trigger signals coordinate the scaling by the multiplier circuits 120, 122. The display rotation phase shifter 142 is set by the user by adjusting the setting on a set of six switches 254 coupled to the phase shifter. A pulse from the first trigger is delayed by anywhere from 1 to 64 clock signals generated by the second trigger input 252. Since the frequency multiplier 140 divides the interval between trigger #1 pulses into 128 equally spaced pulses, a time delay of between 1 and 64 clock signals results in delay of transmission of the first trigger pulse of up to one half of a sleeve rotation. This trigger signal is then transmitted directly to a first phase lock loop circuit 256.

Figure 6:
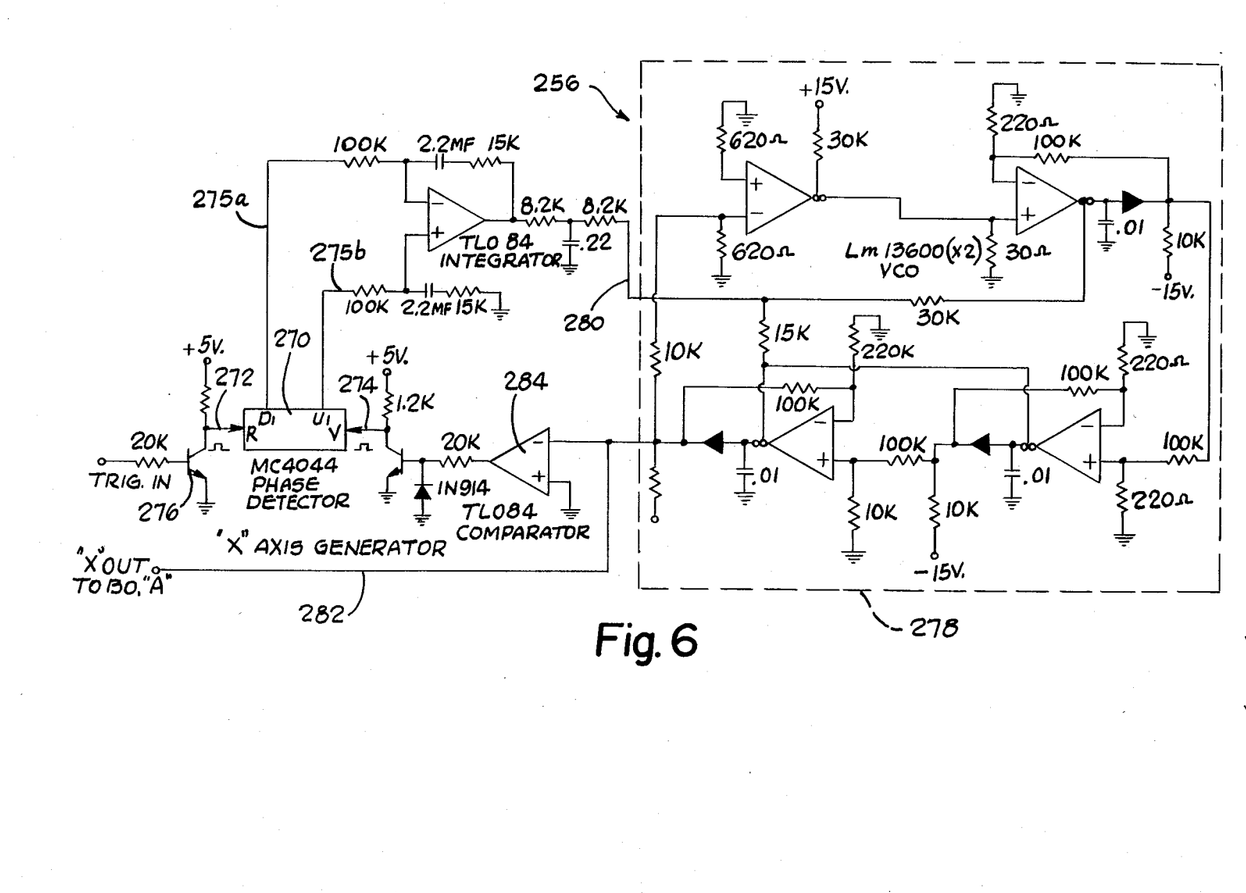

Inserted between a second phase lock loop circuit 258 and the first trigger signal is a delay circuit 260 which in a preferred embodiment delays transmittal of the first trigger signal by 30 clock signals defined by the second trigger input 252. This 30 clock signal delay has been empirically determined to be an appropriate delay to produce a 90 degree phase shift between inputs to the two phase lock loop circuits 256, 258. One of the phase lock loop circuits 256 is illustrated in FIG. 6. It is to be appreciated that a second phase lock loop circuit is identical to this circuit in all respects.

Turning now to FIG. 6, the phase lock loop circuit 256 includes a frequency comparator 270 having two inputs 272, 274. A first input 272 is coupled to the trigger signal through a squaring transistor 276. Internal to the frequency comparator 270 is a mechanism for storing the time interval between receipt of signals at the input 272, 274. The purpose of the frequency comparator is to generate a voltage across its two outputs 275a, b which varies with the frequency of the input 272. The larger the frequency of the signals appearing at this input 272 the larger the voltage output.

A second portion of the phase lock loop circuit shown in FIG. 6 is a sine wave generator 278 which generates a constant amplitude sine wave signal whose frequency is determined by the voltage at an input 280. The FIG. 6 circuitry, thus, receives a series of pulse inputs and converts the pulses into a sinusoidal waveform output 282 in the form of a sine wave having a frequency equal to the frequency of the signal appearing at the input 272. A comparator circuit 284 generates the input 274 to the phase comparator 270. This comparison insures that the frequency of the sine wave generator tracks the frequency of the incoming signals 272. Changes in the input frequency result in a discrepancy between the signals at the two inputs 272, 274 and an adjustment of the output voltage to again cause a match in frequency.

Returning now to FIG. 5, an output from the phase lock loop circuits 256, 258 is selectively coupleable through an inverter circuit 290 depending on the setting of a switch 292. This switch inverts the phase lock loop sinusoidal output and may be necessitated by the signal requirements of a particular oscilloscope's input. A level shift is added to this signal and it is then coupled to an associated multiplier 120 of 122. The level shift cancels a multiplier offset inherent in the MPY 100 integrated circuit multipliers used in a preferred embodiment. These multipliers are commercially available from the Burr-Brown Co., 6730 S. Tuscon Blvd., Tuscon, Az. 85706.

Some of the advantages of the invention may be appreciated with reference to FIGS. 7A–7C and 8A–8C. The waveform in FIG. 8A is a plot of voltage versus time at the input 210 (FIG. 5). An operator viewing this signal on an oscilloscope or the like may not have an idea of the severity or orientation of the flaw that caused this output. When processed by the FIG. 4 circuitry and multiplexed with a shape signal from the amplifier 172 (FIG. 2) however the "X" and "Y" oscilloscope control inputs produce the FIG. 7A representation on the oscilloscope 23. The flaw severity is indicated by the depth of a notch 15a in a circle 17 representing the workpiece surface. The orientation of the notch 15a on the screen gives an indication of the circumferential location of the flaw. This added information is important in analyzing the severity and possible cause of the flaw.

The shape signal 212 is a constant amplitude signal proportional to the workpiece distance to the coil 16. In FIG. 7A the shape signal is used to create an outline 10a for the workpiece. If the workpiece is off center or out-of-round the waveform 10a indicates this fact to an observer. Note that the flaw information to create the notch 15a is not visible on the shape signal generated outline since the selective filtering and gain applied to the flaw output 111a is not performed on the shape output 111b.

Figure 8B:
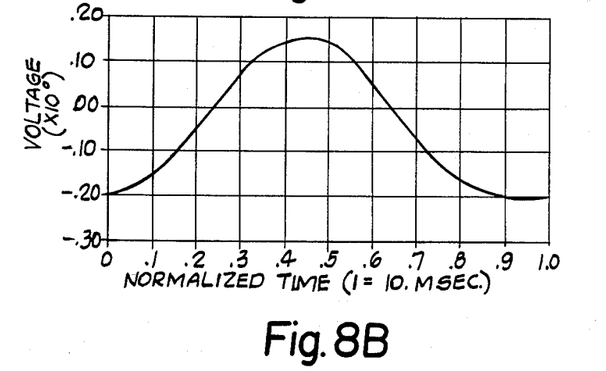
Figure 8C:
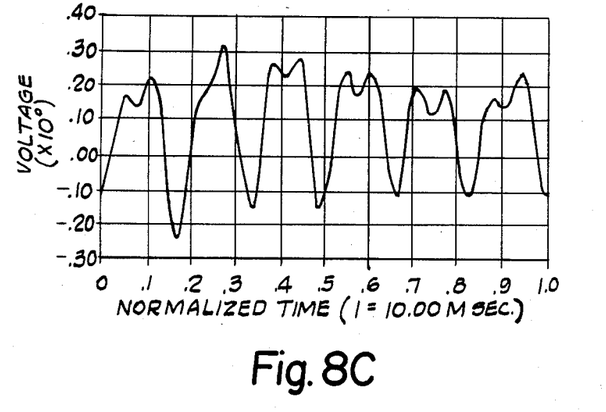

FIGS. 8B and 8C show two additional waveforms output from the amplifier 172 representing shape signals. Again, a user viewing these waveforms would have difficulty confirming the shape of the workpiece. The FIG. 4 circuit transforms these waveforms into the oscilloscope images of FIGS. 7B and 7C. The user can readily determine the image 10b representing the workpiece surface of FIG. 7B is off center and that steps to more properly guide the workpiece should be instituted. In FIG. 7C the user sees a FIG. 10C representing a well centered hex-shaped bar. A user confronted with the task of interpreting the FIG. 8C waveform might not conclude the coils 14, 16 were scanning such a bar.

In both FIGS. 7B and 7C the outline images 17 are generated from flaw signal outputs 111a. When no flaws exist on the workpiece 10 the flaw signal input to the multiplier 118 is a D.C. signal whose size is adjusted by the D.C. voltage source 117. By adjusting this voltage the shape images 10b, 10c are outlined by circular images 17 to give the user a reference for determining an off-center workpiece travel path.

The disclosed oscilloscope images are presented in essentially real time so that what the viewer sees is what is passing through the sleeve beneath the coils 14, 16. This capability fortifies the capability stressed in the previously incorporated Harris et al application to locate problems before a great amount of product has been produced.

Although the present invention has been described with a degree of particularity, it is to be understood that it is the intent that the invention include all modifications and alterations from the disclosed embodiment falling within the spirit or scope of the appended claims.

We claim:

1. Apparatus for testing a metallic workpiece comprising:
   a test coil mounted in proximity to a workpiece and coupled to means for cyclically energizing said coil;
   field modifying means comprising an electrically conductive sleeve defining at least one aperture for selectively modifying a magnetic field created by said coil;
   means coupled to said coil for creating a shape indicating signal related to a distance between an outer workpiece surface and said coil as said magnetic field is modified, and
   means coordinated with said field modifying means for scaling the shape signal to provide an indicating signal which varies with changes in workpiece shape.

2. The apparatus of claim 1 additionally comprising a display coupled to said means for scaling to depict the indicating signal on a display image screen.

3. The apparatus of claim 2 which additionally comprises means for generating a flaw indicating signal coupled to the means for scaling and for displaying said flaw indicating signal on the display image screen.

4. In a flaw detection system having means for producing a flaw signal related to a flaw position on a workpiece, workpiece imaging apparatus comprising:
   means for generating a shape signal varying with a shape of a workpiece outer surface;
   means for time multiplexing said shape and flaw signals;
   scaling means for scaling said time multiplexed signals into component signals relative to a reference; and
   display means for displaying said component signals on an imaging screen to yield a real time image of a workpiece cross-section.

5. The apparatus of claim 4 wherein said flaw detecting system comprises means for rotating a field modifying object comprising a slotted electrically conductive sleeve about said workpiece to enhance said flaw signals and said scaling means includes synchronizing means for determining the angular orientation of said object and creating a timing signal to coordinate scaling of said signals with rotation of said object.

6. The apparatus of claim 5 where said scaling means multiplies said signals by time varying factors which produce orthogonal components of said signal and said display means comprises a video monitor with inputs which respond to said orthogonal components to produce a two dimension representation of a workpiece cross-section.

7. In eddy current testing, a method for displaying an image of a workpiece comprising the steps of:
   positioning a probe coil next to a workpiece path of movement;
   energizing said probe coil with a time varying signal to create an electromagnetic field that induces an eddy current in said workpiece;
   modifying said field by rotating a field modifying object comprising an electrically conductive slotted sleeve around the workpiece;
   monitoring induced signals in said coil due to said eddy currents and generating a first signal related to a presence of a flaw in said workpiece and a second signal related to a distance between the coil and a workpiece surface;
   time multiplexing said first and second signals and scaling said first and second signals by a factor related to an instantaneous position of said rotating object; and
   displaying a visible indication of said cross-section using the scaled first and second signals as control signals to position the indication on a display.

8. The method of claim 7 wherein the motion of said field modifying means is used to coordinate the scaling step with the monitoring step so that said scaling step breaks said first and second signals into components along orthogonal directions for use in positioning said visible indication.

9. Apparatus for imaging a metallic workpiece comprising:
   a test coil mounted in proximity to a workpiece path and coupled to means for cyclically energizing said coil;
   field modifying means comprising an electrically conductive sleeve defining an aperture for selectively modifying a magnetic field created by said coil at time varying locations about a workpiece surface to create a shape indicating signal related to a distance between an outer workpiece surface and said coil; and
   imaging means co-ordinated with said modifying means for displaying an indication of said shape indicating signal as said coil and field modifying means scan the workpiece to present a real time representation of said workpiece surface.

10. The apparatus of claim 9 further comprising means for generating a flaw signal and means to time multiplex the flaw and shape signals on said means for displaying to illustrate the orientation of the flaw about the workpiece.

11. In eddy current testing, a method for displaying an image of a workpiece comprising the steps of:
   positioning a probe coil next to a workpiece path of movement;
   energizing said probe coil with a time varying signal to create an electromagnetic field that induces an eddy current in said workpiece;

modifying said field at varying locations around the workpiece by use of an electrically conductive apertured sleeve;

monitoring signals in said coil induced by said modified field and generating a signal related to a distance between the coil and a workpiece surface; and displaying said signal on a screen to present a visible indication of the shape of the workpiece's outer surface.

12. The method of claim 11 wherein prior to displaying said signal, said signal is scaled by a factor related to the location about the workpiece of said modified field to properly orient said indication on the screen.

13. The method of claim 12 wherein the modification to the field is accomplished by orbiting a field modifying object about the workpiece and said scaling factor is derived from the instantaneous orientation of said object with respect to said workpiece.

14. Apparatus for imaging a metallic workpiece comprising:

a differentially wound test coil having two portions mounted as spaced locations along a workpiece travel path and coupled to means for cyclically energizing said coil;

a rotatably mounted electrically conductive sleeve having apertures at said spaced locations for selectively modifying an electromagnetic field created by said coil portions to produce a flaw indicating signal across said coil portions;

means coupled across one of said coil portions for creating a shape indicating signal related to a distance between an outer workpiece surface and said one coil portion in a region of electromagnetic field modification;

means coordinated with rotation of said sleeve for scaling the shape and flaw signals to provide orthogonal components of said shape and flaw signals, and display means for displaying said orthogonal components of one or the other or both said flaw signals as said coil and field modifying means scan the workpiece.

15. The apparatus of claim 14 wherein said means for scaling comprises a circuit for monitoring rotation of the sleeve and producing two trigger pulses separated in time by approximately 90 degrees of sleeve rotation; and first and second sine wave generators coupled to said trigger pulses to create sine wave scaling signals for scaling said flaw and shape signals.

16. The apparatus of claim 15 which additionally comprises a multiplexer circuit for alternately coupling said shape and flaw signals to said scaling means so that the display means displays first one and then the other of said orthogonal signal components.

17. In eddy current testing, a method for displaying an image of a workpiece comprising the steps of:

positioning a probe coil next to a workpiece path of movement;

energizing said probe coil with a time varying signal to create an electromagnetic field that induces an eddy current in said workpiece;

modifying said field by rotating a field modifying object comprising an electrically conductive sleeve defining at least one aperture around the workpiece, and monitoring induced signals in said coil due to said eddy currents and generating a signal related to a distance between the coil and a workpiece surface at the region the field is modified.

* * * * *